United States Patent [19]

Take et al.

[11] Patent Number: 4,984,469

[45] Date of Patent: Jan. 15, 1991

[54] AMPLITUDE MEASUREMENT DEVICE FOR VISCOELASTICITY ANALYSIS

[75] Inventors: Masafumi Take; Haruo Takeda; Nobutaka Nakamura, all of Tokyo, Japan

[73] Assignee: Seiko Instruments, Inc., Chiba, Japan

[21] Appl. No.: 437,224

[22] Filed: Nov. 16, 1989

[30] Foreign Application Priority Data

Nov. 21, 1988 [JP] Japan .................................. 63-294233

[51] Int. Cl.$^5$ ................................................ G01L 1/00
[52] U.S. Cl. .......................................................... 73/770
[58] Field of Search ................... 324/130, 131; 73/763, 73/765, 769, 770, 789, 790, 794–797, 806, 808

[56] References Cited

U.S. PATENT DOCUMENTS

| | | | |
|---|---|---|---|
| 3,477,286 | 11/1969 | Baker | 73/770 |
| 3,712,125 | 1/1973 | Meyer | 73/794 |
| 4,145,933 | 3/1979 | Imig et al. | 73/770 |
| 4,414,852 | 11/1983 | McNeill | 73/769 |

FOREIGN PATENT DOCUMENTS

| | | | |
|---|---|---|---|
| 0022986 | 2/1977 | Japan | 73/797 |
| 0680311 | 10/1952 | United Kingdom | 73/770 |

*Primary Examiner*—Robert Raevis
*Attorney, Agent, or Firm*—Spensley Horn Jubas & Lubitz

[57] ABSTRACT

An apparatus for providing an indication of the amplitude of a length signal having a top peak, a bottom peak and an intrinsic offset and being indicative of viscoelasticity of a sample. A peak measurement circuit is provided for measuring values of top and bottom peaks of the length signal to determine the amplitude thereof and an offset circuit is connected for providing a compensative offset. An adder circuit is provided for adding the compensative offset to the length signal. An offset calculation circuit receptive of the values of the top and bottom peaks from the peak measurement circuit is provided for outputting to the offset circuit, according to the received values, a control signal effective to control the offset circuit to provide an update compensative offset effective to cancel the intrinsic offset of the length signal.

2 Claims, 1 Drawing Sheet

AMPLITUDE MEASUREMENT DEVICE FOR VISCOELASTICITY ANALYSIS

BACKGROUND OF THE INVENTION

The present invention relates to measurement of the amplitude of a length signal in viscoelasticity analysis of a sample.

In the prior art as shown in FIG. 3 the amplitude of a length signal is maintained sufficiently smaller than the effective measurement range of a peak measurement circuit and the amplitude is measured while it contains an offset.

The above-noted prior art has the drawback that a major part of the effective measurement span of the peak measurement circuit is provided for the offset, which thereby impairs the accuracy of the measurement of the amplitude.

SUMMARY OF THE INVENTION

An object of the present invention is to eliminate the offset contained in the length signal to thereby remove the above-noted drawback.

The above and other objects are achieved, according to the invention, by an amplitude measurement device for viscoelasticity analysis composed of a peak measurement circuit for measuring a peak of a length signal, an offset circuit for providing a compensative offset in relation to the length signal, an adder circuit for adding or subtracting the compensative offset to or from the length signal, and an offset calculation circuit for receiving an output signal from the peak measurement circuit and outputting, according to the output signal, to the offset circuit a control signal effective to update the compensative offset to cancel an intrinsic offset contained in the length signal.

In operation of the device, the length signal is inputted into the adder circuit in which the length signal is added with a compensative offset and the thus obtained input signal is inputted into the peak measurement circuit. The peak measurement circuit measures the top and bottom peaks of the input signal and outputs the measured values to the offset calculation circuit. The offset calculation circuit calculates a center value of the input signal according to the values of the top and bottom peaks. The offset calculation circuit further compares the center value of the input signal with a center level of an effective measurement range of the peak measurement circuit.

The offset calculation circuit operates when a difference exists between the center value of the input signal and the center level of the measurement circuit range to output a control signal representative of the difference value plus the current compensative offset value which is currently being applied to the offset circuit. The offset circuit applies an updated compensative offset according to the value from the offset calculation circuit to the adder circuit so as to eliminate the difference between the center value of the input signal and the center level of the measurement range of the peak measurement circuit so that the peak measurement circuit is supplied with an input signal free of any offset. Consequently, even when the center value of the length signal fluctuates due to expansion of the sample and/or creep, the measurement of the amplitude of the length signal can be effected with high accuracy.

DESCRIPTION OF THE PREFERRED EMBODIMENTS

Figure 1:
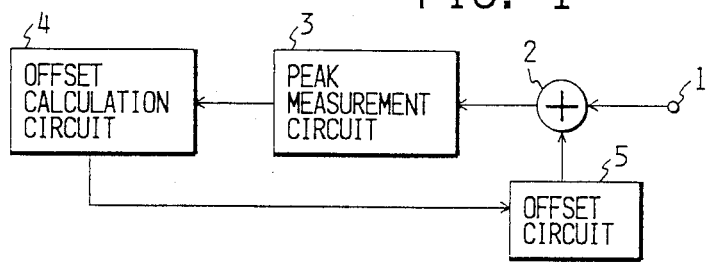
FIG. 1 is a circuit block diagram showing one embodiment of the present invention.

An embodiment of the present invention is described herein after with reference to the drawings in detail. FIG. 1 shows an amplitude measurement device provided in a viscoelasticity analysis apparatus. The viscoelasticity analysis of a sample is carried out such that a sinusoidal stress is applied to the sample to cause a sinusoidal strain, and the amplitude and phase of the sinusoidal strain are measured and compared with those of the sinusoidal stress to thereby determine the viscoelasticity of the sample. The amplitude measurement device is provided to measure the amplitude of the sinusoidal strain.

Referring to FIG. 1, the amplitude measurement device is composed of an adder circuit 2 having a first input connected to an input terminal 1 receptive of a length signal which is representative of the sinusoidal strain of a sample, the adder circuit having a second input connected to the output of an offset circuit 5 and having an output connected to the input of a peak measurement circuit 3. An offset calculation circuit 4 is connected between the peak measurement circuit 3 and the offset circuit 5.

Figure 2:
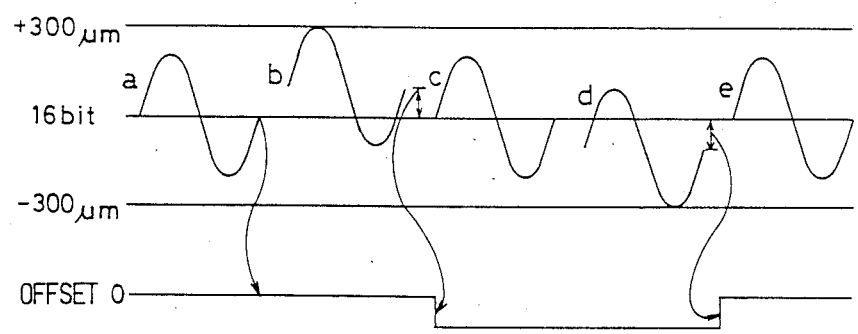
FIG. 2 is a waveform diagram illustrating operation of the FIG. 1 embodiment.
Figure 3:
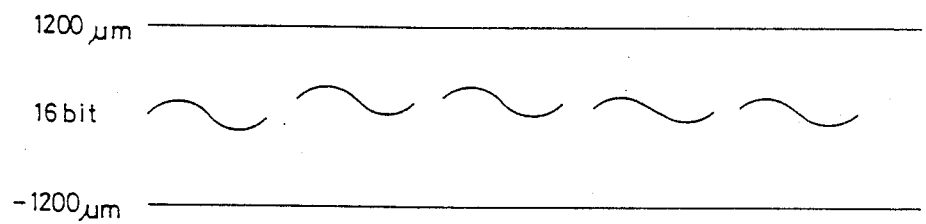
FIG. 3 is a waveform diagram of the operation of a prior art measurement device.

The input terminal 1 receives a length signal having an amplitude representing the instantaneous deviation in the length of a sample from a reference value. Thus, for example, a length signal b having top peak value of $+300\ \mu m$ and bottom peak value of $-100\ \mu m$ is shown in FIG. 2. At this time, the offset circuit 5 is outputting, for example, an initial compensative offset signal having an offset value of $0\ \mu m$ which was the offset value calculated for the preceding length signal, a. The output from circuit 5 is supplied to the adder circuit 2 so that the length signal b is applied to the peak measurement circuit 3 as an input signal in which the top peak value of $+300\ \mu m$ and bottom peak value of $-100\ \mu m$ are measured to determine the signal amplitude and the measured results are outputted to the offset calculation circuit 4. The offset calculation circuit 4 calculates the center value of $+100\ \mu m$ of the input signal according to its top and bottom peak values, and outputs a control signal having a value of $-100\ \mu m$, effective to cancel the center value of $+100\ \mu m$, to the offset circuit 5. The offset circuit 5 then applies an updated compensative offset signal having the value of $-100\ \mu m$ to the adder circuit 2 to produce the next input signal c which is inputted to the peak measurement circuit 3 so that the intrinsic offset of the length signal b is eliminated.

Next, when another length signal having peak values corresponding to those of signal a is applied to the input terminal 1, the adder circuit 2 feeds an input signal d containing the offset signal value $-100\ \mu m$ provided by the offset circuit 5 to the peak measurement circuit 3, which measures a top peak value of $+100\ \mu m$ and a bottom peak value of $-300\ \mu m$ of the input signal d, and the measured results are fed to the offset calculation circuit 4. The offset calculation circuit 4 calculates the center value of $-100\ \mu m$ of the input signal d according to the measured top and bottom peak values and outputs a new control signal having a value of 0 μm which is the sum of the value of −100 μm currently applied to the offset circuit 5 and the value of +100 μm effective to cancel the calculated central value of −100 μm into the offset circuit 5. Then, the peak measurement circuit 3 receives an input signal e which is identical to the length signal a applied to the input terminal 1 so that the offset is eliminated from the signal supplied by adder circuit 2.

Accordingly, even when the input terminal 1 receives a length signal having a drifting offset due to expansion of a sample and creep, the amplitude measurement device carries out repeatedly the abovedescribed feedback operation to thereby enable highly accurate amplitude detection effectively utilizing the available measurement range of the peak measurement circuit 3.

As described above, according to the present invention, since the device is constructed to remove offsets of the input signal, measurement of the amplitude free of the offset can be effectively and accurately carried out throughout the measurement range of the peak measurement circuit. Further, the invention is applicable to a phase detection circuit when a zero-crossing signal is utilized as well as to the amplitude measurement device. Moreover, the offset calculation circuit can be implemented by a microprocessor and the length signal can be a 16-bit digital signal.

This application relates to subject matter disclosed in Japanese Patent Application No. 63-294233, filed Nov. 21, 1988, the disclosure of which is incorporated herein by reference.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. An apparatus for providing an indication of the amplitude of a length signal having a top peak, a bottom peak and a center value, the length signal being indicative of the viscoelasticity of a sample, comprising:
   an offset circuit for providing a compensative offset signal;
   an adder circuit connected for receiving the length signal and the compensative offset signal and for producing an output signal having a value representative of the sum of the length signal and the compensative offset signal;
   a peak measurement circuit connected to receive the output signal produced by said adder circuit for measuring the values of the top and bottom peaks of the output signal to determine the amplitude of the length signal; and
   an offset calculation circuit connected for receiving the values of the output signal top and bottom peaks from said peak measurement circuit and for supplying to said offset circuit a control signal effective to cause the offset signal provided by said offset circuit to have a value which compensates for deviations of the center value of the length signal from a desired value.

2. An apparatus as defined in claim 1 wherein said peak measurement circuit has an effective measurement range with a center level and the control signal supplied by said offset calculation circuit causes the offset signal to have a value which gives the output signal from said adder circuit a center value corresponding to the center level of the measurement range of said peak measurement circuit.

* * * * *